United States Patent [19]
Battersby et al.

[11] Patent Number: 5,614,487
[45] Date of Patent: Mar. 25, 1997

[54] SUSTAINED RELEASE PHARMACEUTICAL COMPOSITION

[75] Inventors: John E. Battersby, So. San Francisco; Ross G. Clark, Pacifica; William S. Hancock, Hillsborough, all of Calif.

[73] Assignee: Genentech, Inc., So. San Francisco, Calif.

[21] Appl. No.: 69,146

[22] Filed: May 28, 1993

[51] Int. Cl.⁶ .................................................. A61K 38/16
[52] U.S. Cl. ................................. 514/2; 514/12; 530/402; 530/399; 424/488
[58] Field of Search .......................... 514/8, 12; 530/402, 530/412, 399; 424/488

[56] References Cited

U.S. PATENT DOCUMENTS

| | | | |
|---|---|---|---|
| 3,947,352 | 3/1976 | Cuatrecasas | 210/31 |
| 4,003,792 | 1/1977 | Mill et al. | 424/89 |
| 4,179,337 | 12/1979 | Davis et al. | 435/181 |
| 4,446,316 | 5/1984 | Chazov et al. | 536/112 |
| 4,452,773 | 6/1984 | Molday | 424/1.1 |
| 4,585,754 | 4/1986 | Meisner et al. | 514/8 |
| 4,745,180 | 5/1988 | Moreland et al. | 530/351 |
| 4,857,505 | 8/1989 | Arendt | 514/2 |
| 5,130,255 | 7/1992 | Battersby et al. | 436/86 |

FOREIGN PATENT DOCUMENTS

| | | |
|---|---|---|
| 0372752 | 6/1990 | European Pat. Off. . |
| 9001332 | 2/1990 | WIPO . |

OTHER PUBLICATIONS

Juliano, R. L., "Drug Delivery Systems, Characteristics and Biomedical Applications", *Oxford University Press*, New York, pp. 258–312 (1980).
Langer, R. S., et al., "Medical Applications of Controlled Release", *CRC Press*, Inc., Florida, 1:109 (1984).
Lee, P. I., et al., "Controlled–Release Technology, Pharmaceutical Applications", *American Chemical Society Symposium Series 348*, Wash. D. C., pp. 188–200 (1987).
Bernstein, A., et al., "Higher Antitumor Efficacy of Daunomycin When Linked To Dextran:In Vivo and In Vitro Studies", *J. Natl. Cancer Inst.*, 60:379 (1978).
Odya, C. E., et al., "Soluble Dextran Complexes of Kallikrein, Bradykinin and Enzyme Inhibitors", *Biochemical Pharmacology*, 27:173 (1978).
Jentoft, N., et al., "Protein Labeling by Reductive Alkylation", *Methods in Enzymology*, 91:570 (1983).
Dixon, H. B. F., "N–Terminal Modification of Proteins—A Review", *Journal of Protein Chemistry*, 3:99 (1984).
Tuma, D. J., et al., "Enhancement of Acetaldehyde–Protein Adduct Formation by L–Ascorbate", *Archives of Biochemistry and Biophysics*, 234:377 (1984).
Molteni Meth Enz 112, 285, 1985.
Wagner and Zook, *Synthetic Organic Chemistry*, John Wiley and Sons Inc., N.Y. 1953, p. 728.

*Primary Examiner*—David Lukton
*Attorney, Agent, or Firm*—Walter H. Dreger

[57] ABSTRACT

The present document discloses the formation of imine adducts, preferably between a primary amine of a biologically active polypeptide and a reactive aldehyde group of a physiologically acceptable carrier. The imine adduct of human growth hormone and dextran is specifically described. These adducts serve to release the biologically active polypeptide via the reversible reaction in the formation of the imine adduct bond. These adducts have a surprising degree of stability that permits the use of the complex as a sustained release preparation. A key advantage of this technology is that after hydrolysis the complex releases the unmodified pharmaceutical. Thus, these adducts can be used as pharmaceutical compositions useful for the sustained release of the biologically active polypeptide over a predetermined, desired period of time.

3 Claims, 8 Drawing Sheets

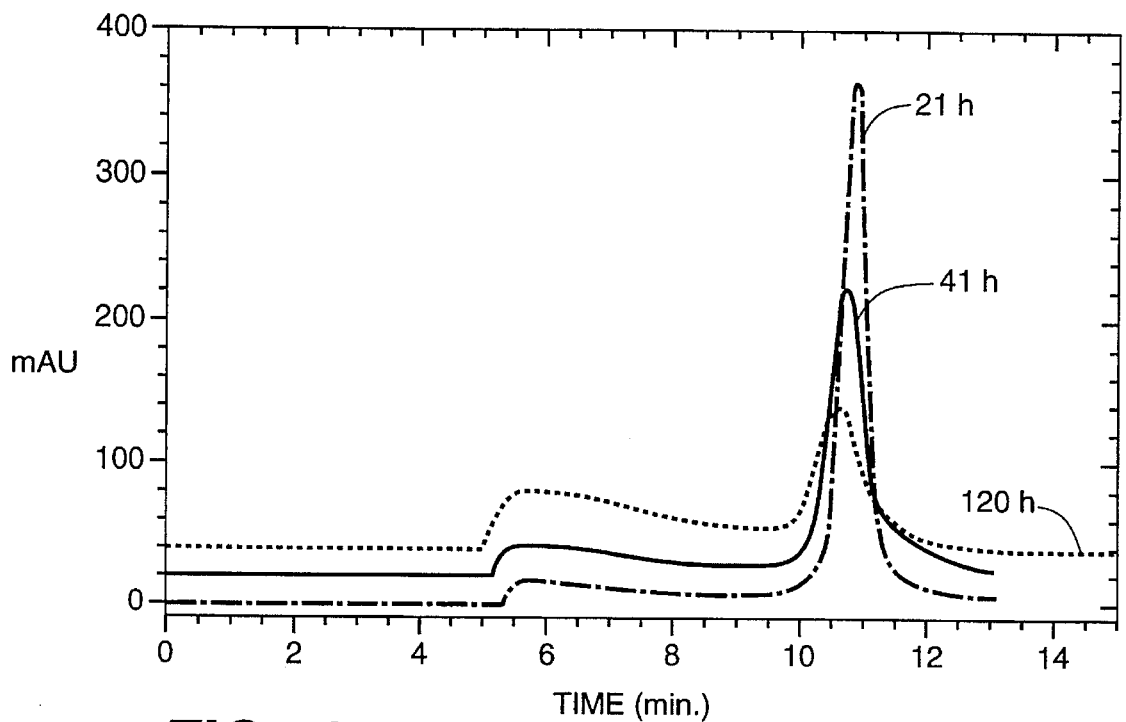
FIG._1
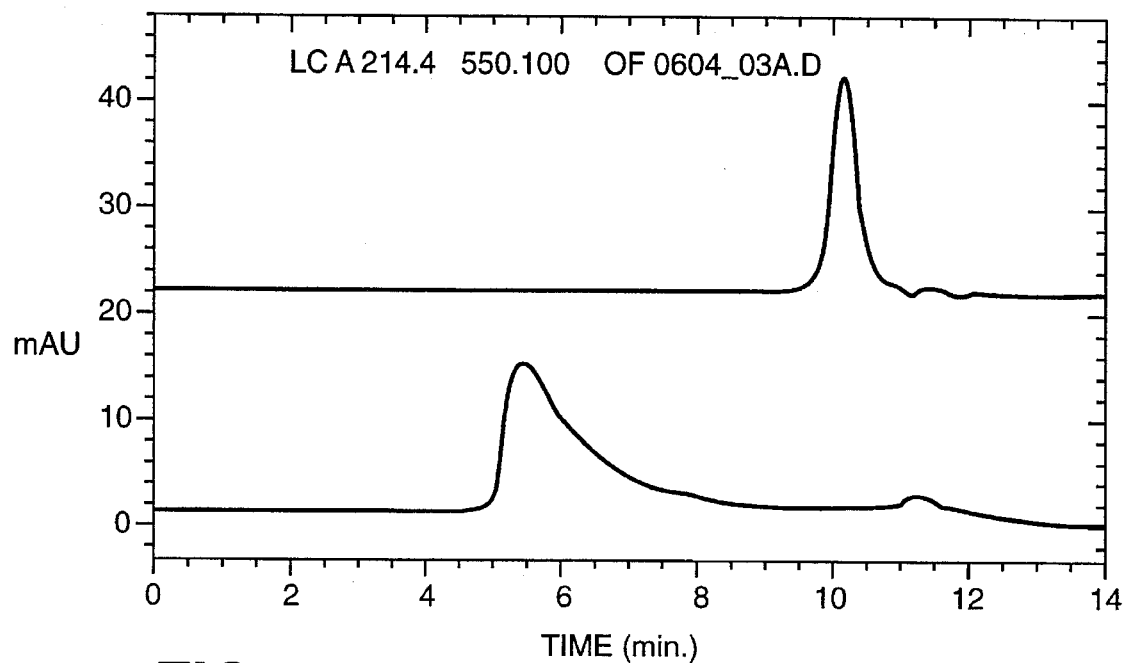
FIG._3

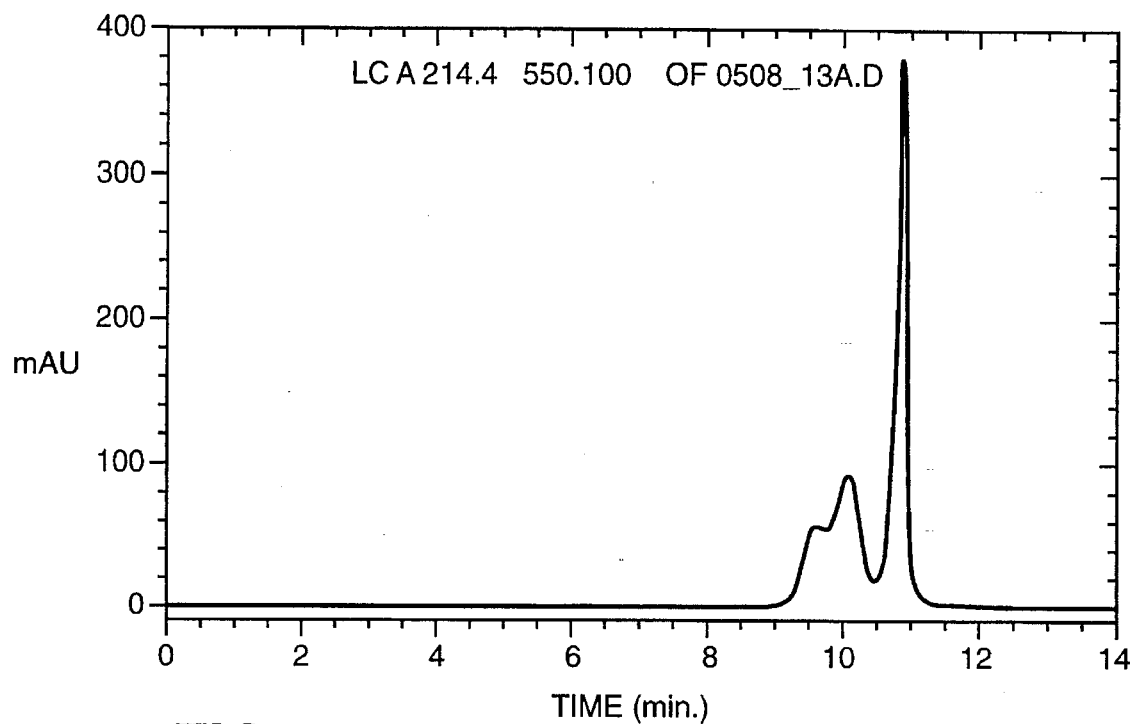
FIG._2A
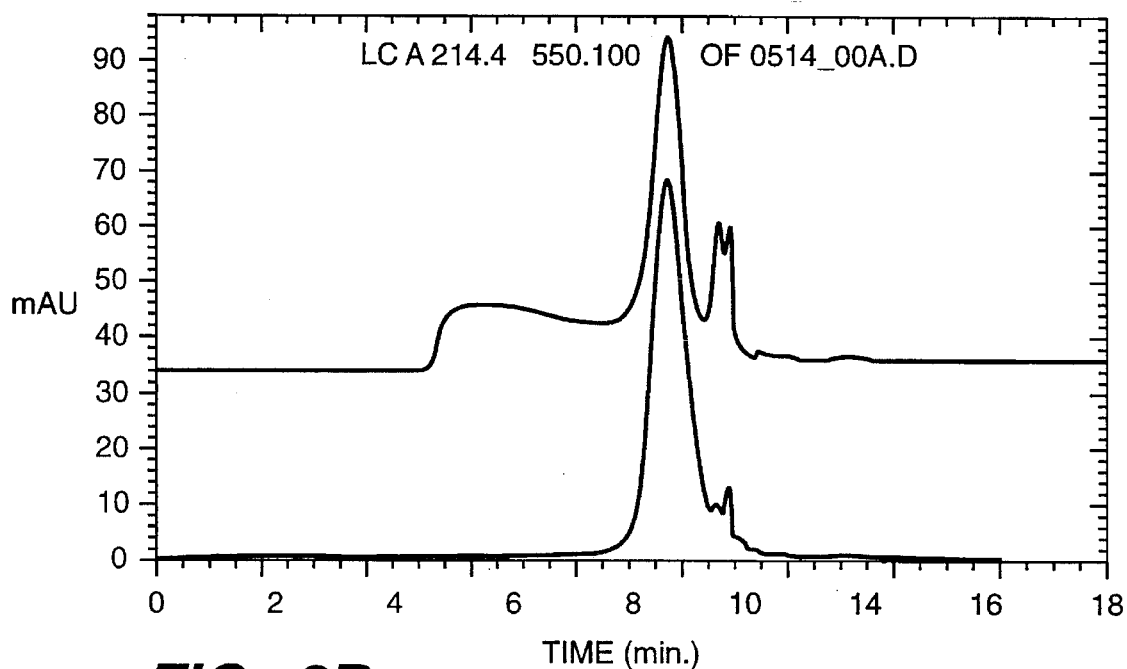
FIG. 2B

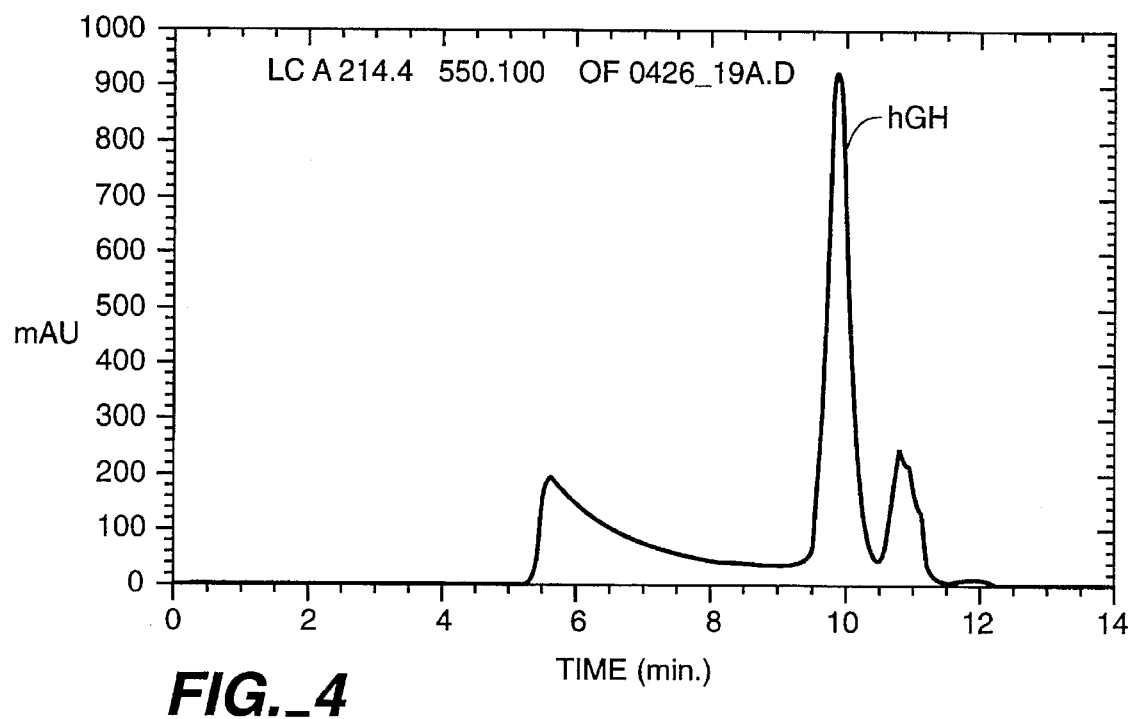
FIG._4
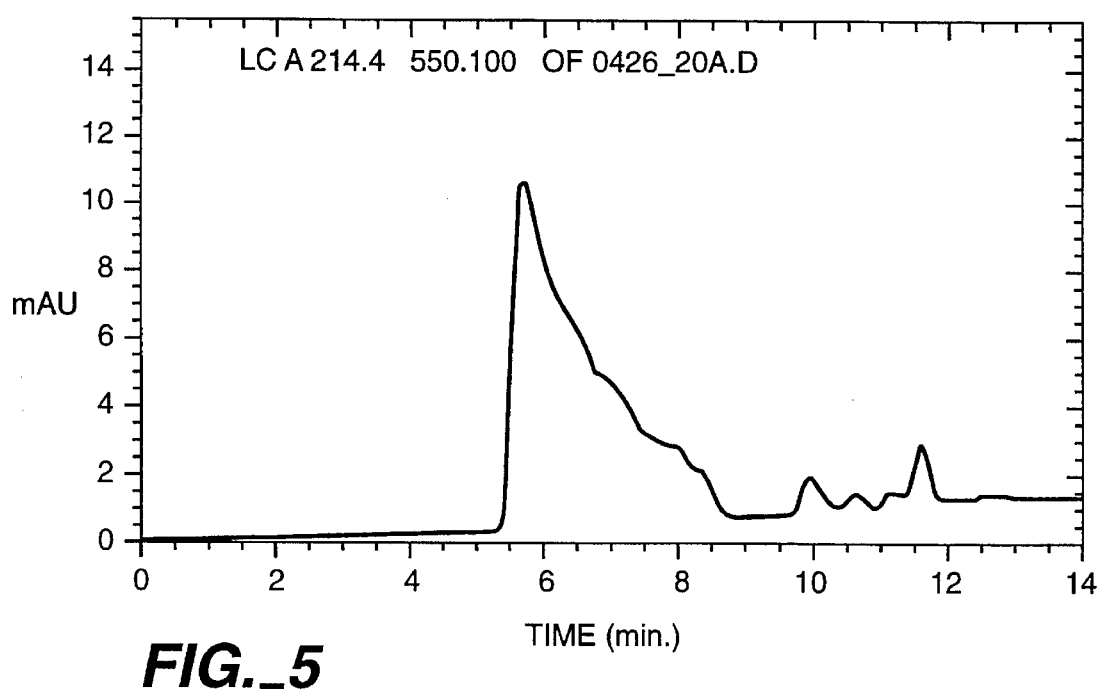
FIG._5

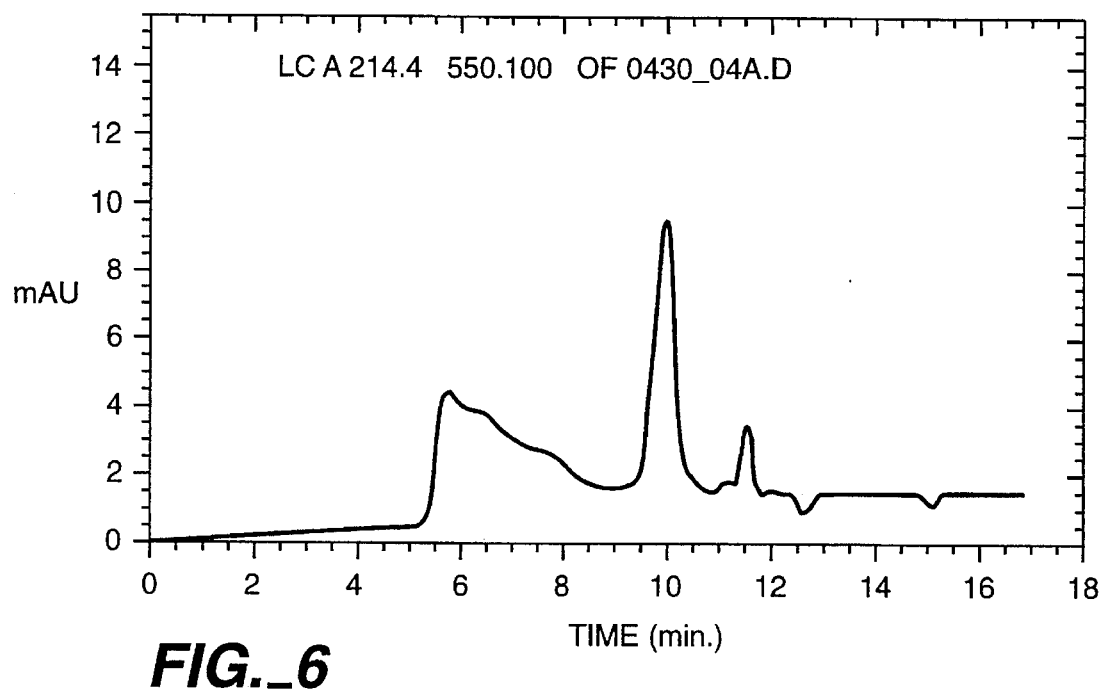
FIG._6
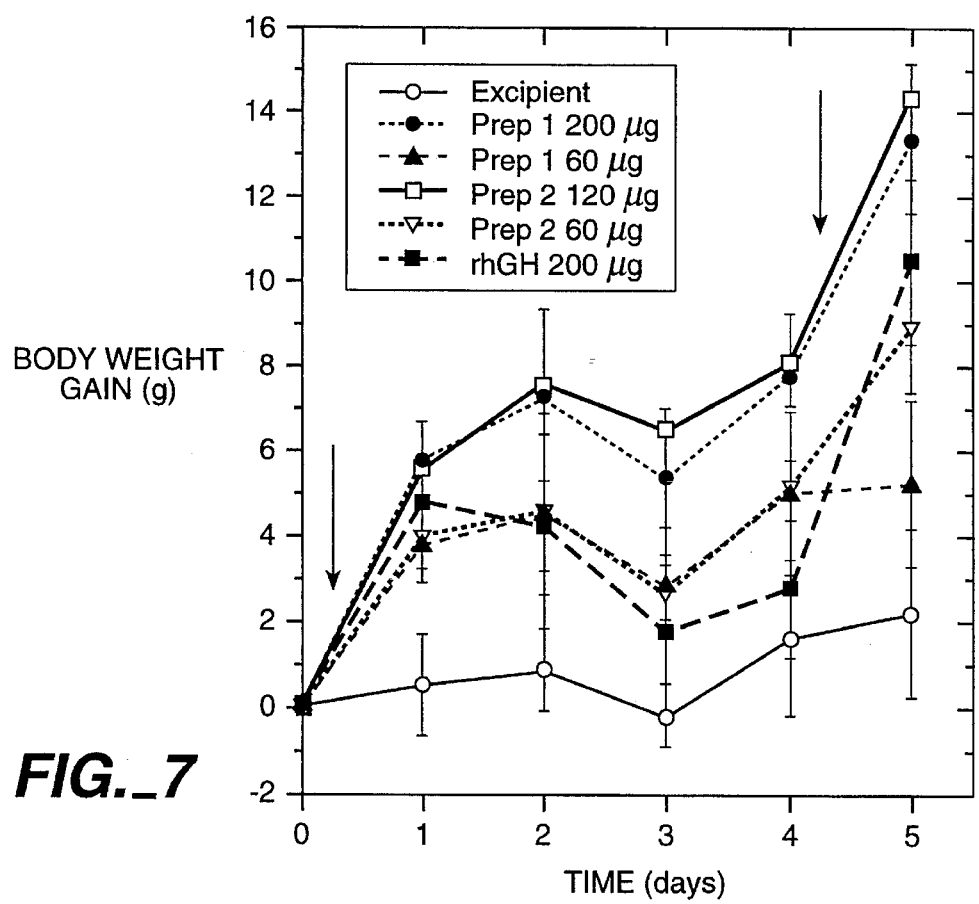
FIG._7

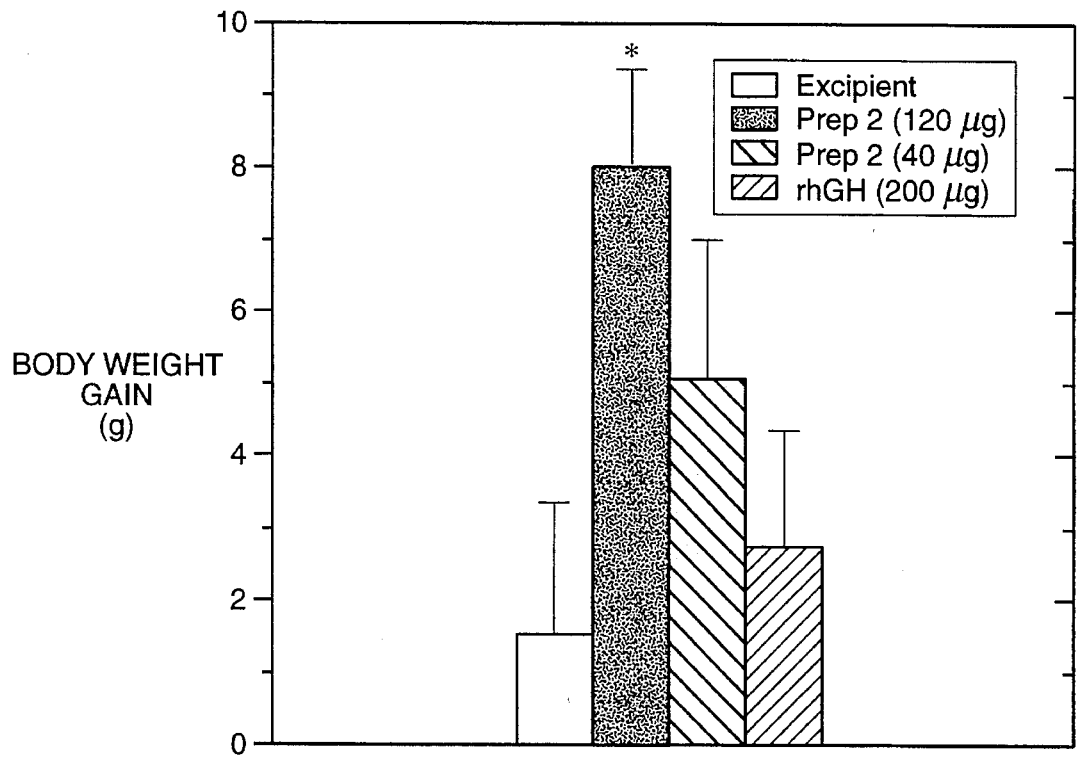
FIG._8
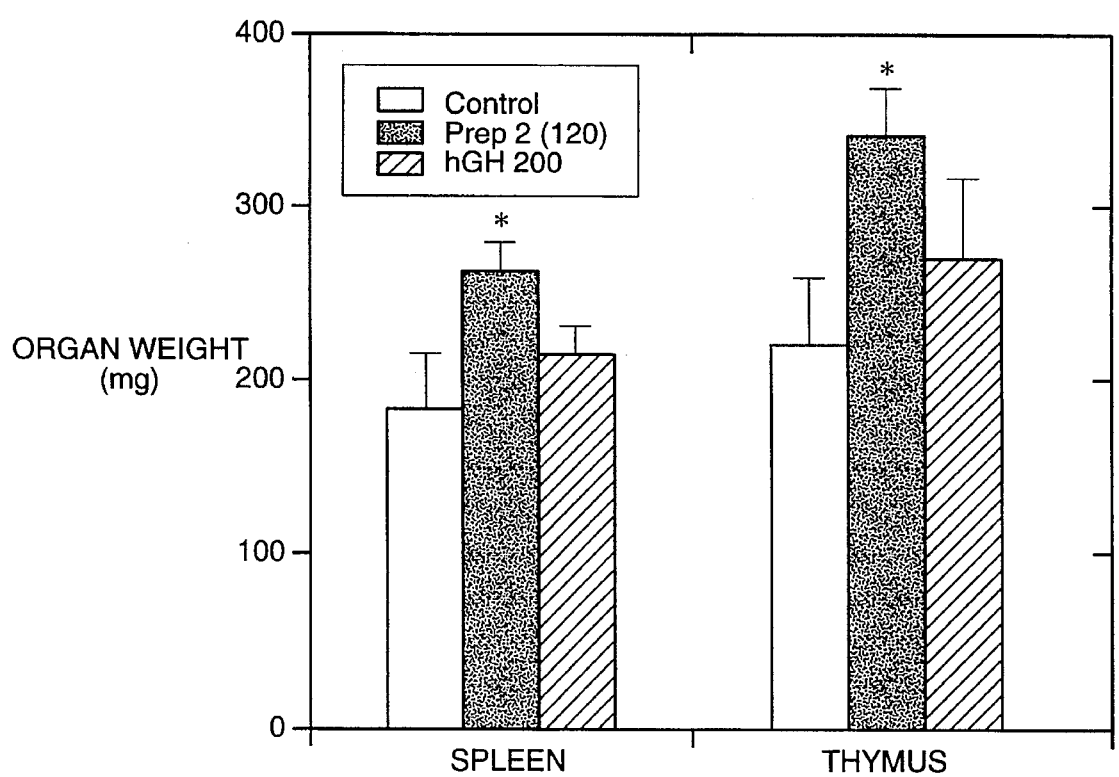
FIG._9

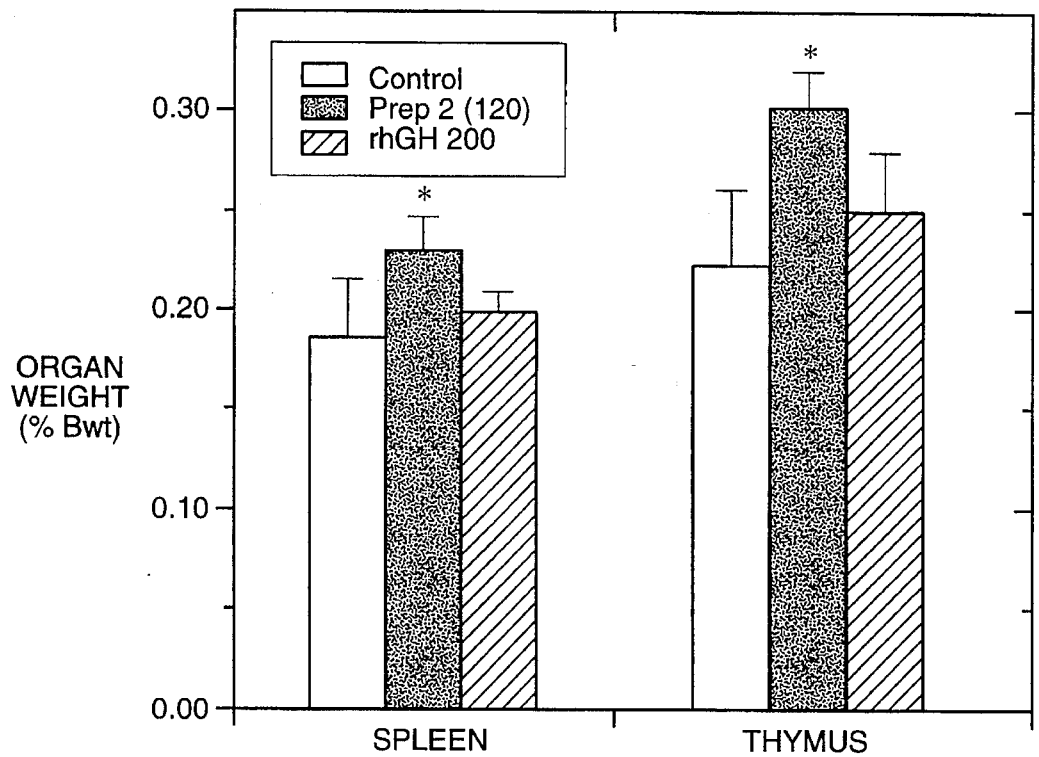
FIG._10
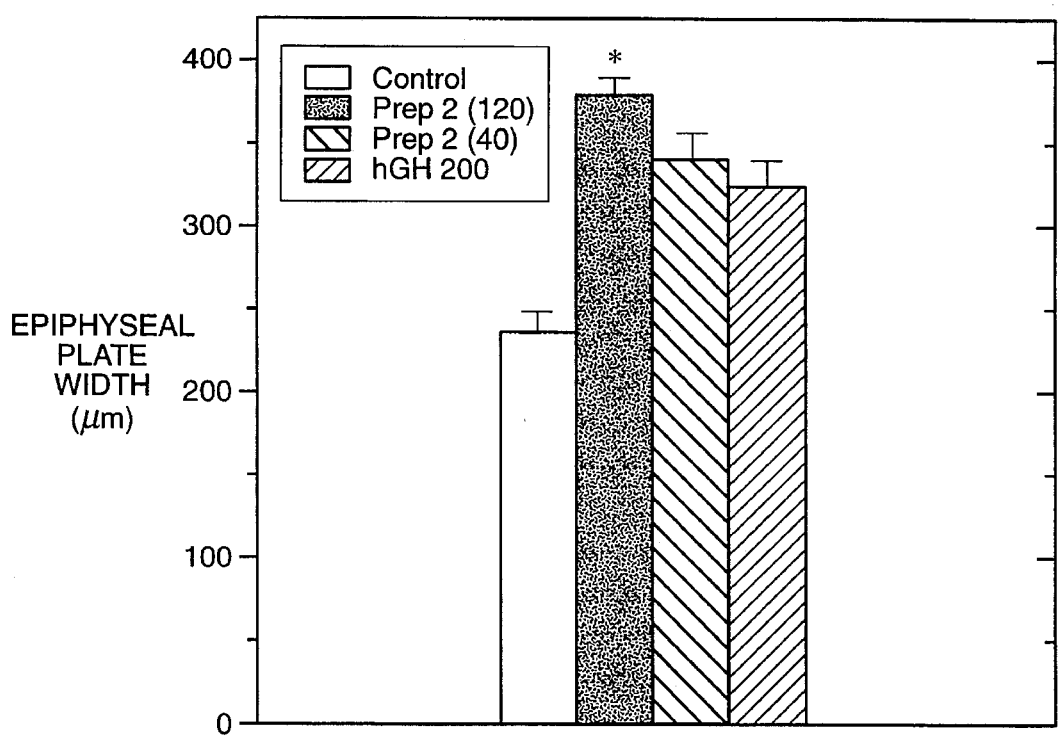
FIG._11

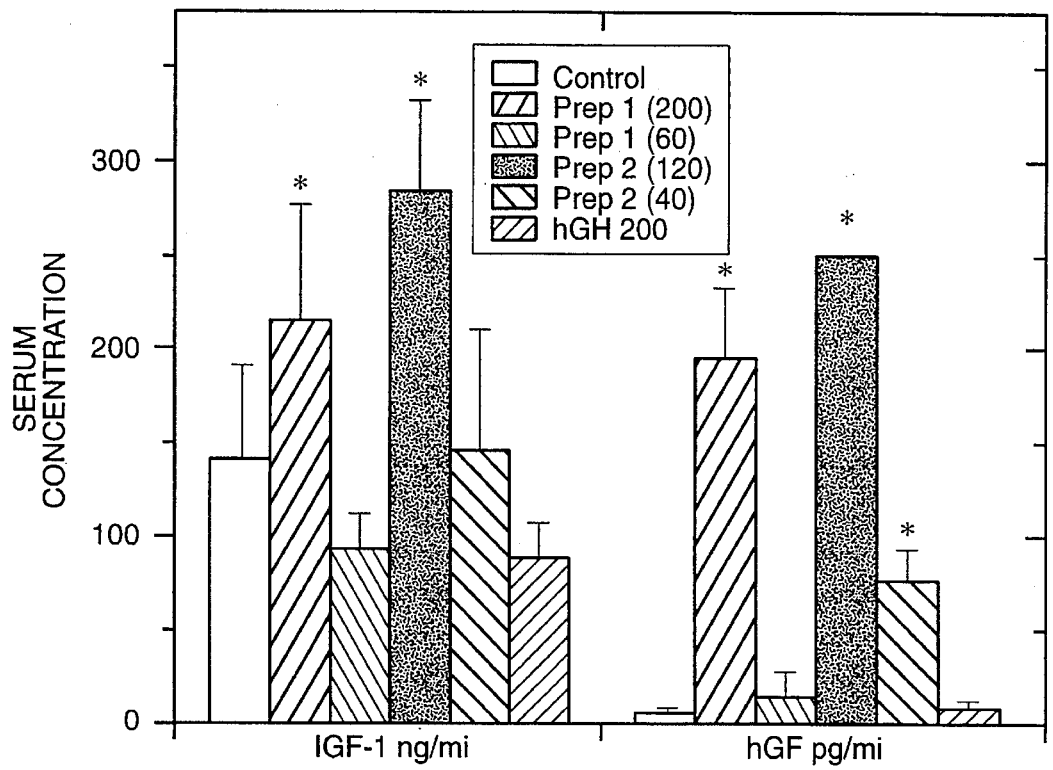
FIG._12
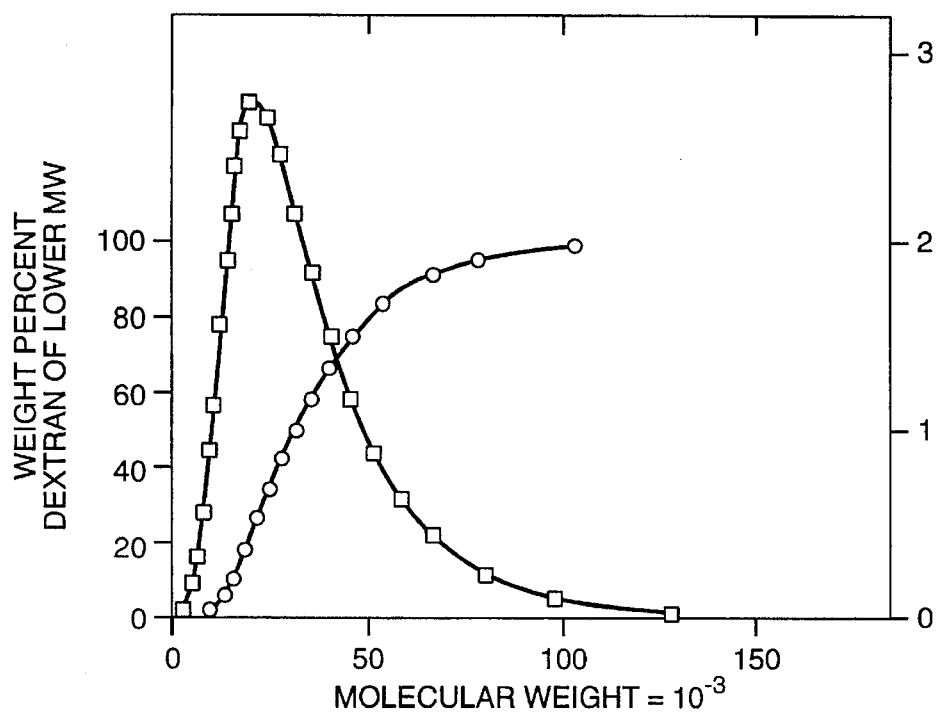
FIG._13

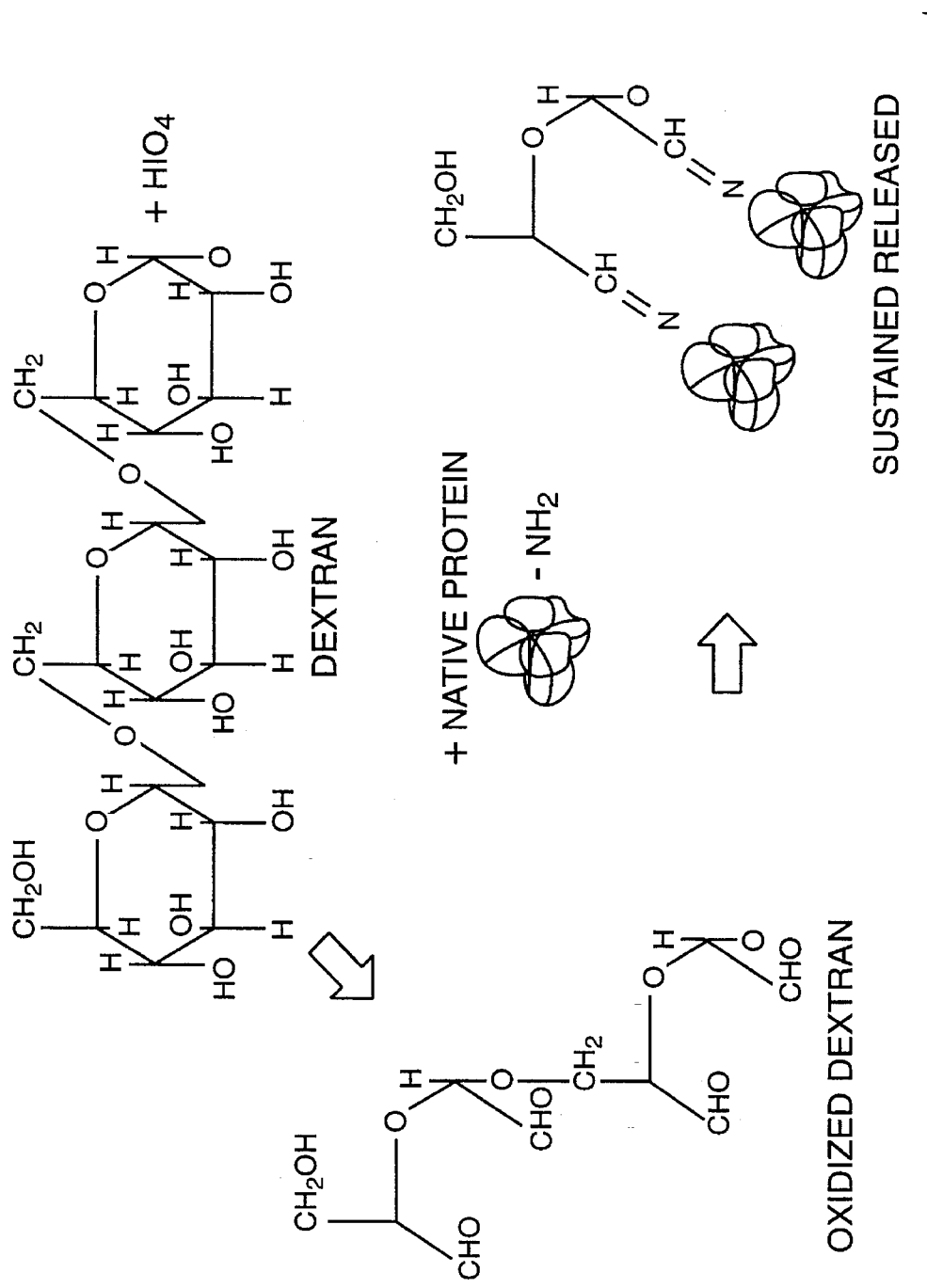
FIG._14

SUSTAINED RELEASE PHARMACEUTICAL COMPOSITION

FIELD OF THE INVENTION

The present application is directed to sustained release pharmaceutical compositions of biologically active polypeptides. The compositions hereof are physiologically acceptable and feature an imine adduct of the biologically active polypeptide with a carrier molecule that functions to facilitate the release of the unmodified biologically active polypeptide as such over a sustained period of time.

BACKGROUND OF THE INVENTION

There are a number of diverse methods that have been suggested and implemented for the release of drugs over a sustained period of time in vivo. Many of these involve the physical entrapment of the drug by the fashioning of unique dosage forms that include enteric coatings, microencapsulation and so forth.

Another example utilizes polyethyleneglycol (PEG) irreversibly covalently linked to a polypeptide. Potential drawbacks with this system are that it may be immunogenic, and the PEG units may mask the polypeptide, effectively removing it from recognition by its receptor or otherwise interfering with its normal in vivo expression of biological activity.

Other methods involve the use of polysaccharides as drug carriers, reaction of bioactive agents with preformed polymers, and the use generally of carriers to carry the drug entity and deliver it variously over sustained periods in vivo. These methods generally involve irreversible chemical modifications of the polypeptide with predictable, and perhaps undesirable biological consequences. Attention in this regard is directed to *Drug Delivery System*, edited by Juliano, Oxford University Press, New York (1980); *Medical Applications of Controlled Release*, Vol. 1, editors Langer and Wise, CRC Press, Inc., Boca Raton, Fla. (1984), and *Controlled Release Technology*, Pharmaceutical Applications, editors Lee and Good, American Chemical Society, Washington, D.C. (1987).

Bernstein, et al., in *J. National Cancer Institute* 60, 379 (1978) coupled daunomycin with dextrans of various molecular sizes. In each instance, the unstable link of the antibiotic with the aldehyde of the oxidized dextran was immediately stabilized by reduction with sodium borohydride.

The foregoing dextran coupling is reported in the aforementioned *Drug Delivery Systems* text where there are references to several researchers in the area, using dextrans as carriers and more particularly periodate oxidation as the conjugation method (see particularly pages 261, 262 and 290 et seq.).

Odya, et al., one group of the cited researchers, [*Biochemical Pharmacology* 27, 173 (1978)], refers to the couplings of a number of polypeptides with oxidized dextran. In each case, subsequent treatment with sodium borohydride served to reduce both the reactive aldehyde groups remaining on the dextran and the unstable adduct formed when the proteins reacted with the aldehyde groups, resulting from the oxidized dextran, to produce stable secondary amines.

The reaction described in the foregoing references is known and is referred to commonly as reductive alkylation as a convenient method for converting amino groups in polypeptides to their alkylamine derivatives through the reduction of the adduct that forms between the amino groups and aldehydes as shown by the following reaction:

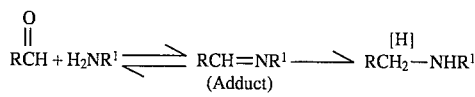

This reaction is also described, for example, by Jentoft et el., *Methods in Enzymology* 91, 570 (1983) and in U.S. Pat. No. 3947352 (see particularly FIG. 2).

U.S. Pat. No. 4745180 and patent application WO 90/01332 describe polypeptide-heparin conjugates wherein the polypeptide is described as being covalently bonded via one or more lysine residues to heparin, and more particularly through the free epsilon amino group of the lysine group. This conjugation is brought about by the reactive aldehyde group of the heparin fragment forming the labile adducts that, as referred to above, are converted into stable secondary amines under reducing conditions.

These latter applications demonstrate the collective convention that because the intermediate imine conjugates (adducts) were inherently unstable—being labile under neutral aqueous solutions not unlike physiological conditions—they were to be avoided. Hence, they were eliminated by reduction (hydrogenation).

SUMMARY OF THE INVENTION

The present invention provides sustained release pharmaceuticals and pharmaceutical compositions thereof. The pharmaceutical comprises an imine adduct of a biologically active polypeptide, such as human growth hormone, with a carrier moiety. A primary amine of one is reacted under non-reducing conditions with a reactive aldehyde of the other to form an imine bond, such that the resultant pharmaceutical product has the following structure:

$$R\text{-CH=N-}R^1$$

wherein R and $R^1$ are the remainders of the carrier and the polypeptide. The reaction is reversible (an equilibrium reaction) and the resultant adduct bears the imine bond (-CH=N-) that over time attends the release of the unmodified biologically active polypeptide as such.

In a preferred embodiment, the amine reactant is the N-terminal amine (or primary amine of a backbone amino acid) of the biological polypeptide of interest and the aldehyde is attached to the carrier.

In a reverse embodiment, the aldehyde group may be available from activation of a sugar moiety of a glycoprotein and the amine group from the carrier, or from an activated sugar moiety attached to another biological molecule such as a glycolipid.

In a further embodiment, two polypeptides could be so linked, one or both being a glycoprotein.

Thus, the carrier-polypeptide imine adducts are sustained release pharmaceuticals due to the reversible character of the reaction by which such adducts are formed.

Such sustained release pharmaceuticals can be formulated into sustained release pharmaceutical compositions by admixing them with pharmaceutically acceptable excipients and the resultant compositions are administrable so as to provide release of the unmodified biologically active polypeptide as such over a sustained period of time for desired pharmacological effect in vivo.

The present invention is directed to such sustained release pharmaceuticals and pharmaceutical compositions. The present invention is further directed to a method of imparting sustained release of a polypeptide as such in vivo by administering a sustained release pharmaceutical composition defined above. The present invention is further directed to a method of treating an individual over a sustained period of time in vivo by administering a sustained release pharmaceutical composition as defined above.

The present invention is further directed to a method for preparing a sustained release pharmaceutical which comprises reacting a reactive aldehyde group, in a preferred embodiment of an activated (oxidized) carrier with a primary amine, in the preferred embodiment of a biologically active polypeptide, under non-reducing conditions to form an imine bond between said carrier and said biologically active polypeptide, and isolating said pharmaceutical product, and optionally formulating such isolated pharmaceutical with a pharmaceutically acceptable excipient to obtain a sustained release pharmaceutical composition.

The present invention is directed to the predicate of forming such imine conjugates of a carrier with a biologically active polypeptide in all of its associated aspects. Thus, in a further aspect, one may cause the imine binding of one or a plurality of biologically active polypeptides with a carrier, so as to release in vivo over a sustained period of time a number of biologically active polypeptides through the inevitable reversible reaction of the conjugate releasing the polypeptides. This would conveniently provide so-called cocktail regimens where synergistic properties could be exploited in vivo, for example, human growth hormone and IGF-1 in the treatment of AIDS.

One can additionally fashion conjugates wherein a first polypeptide is bonded followed by hydrogenation to irreversibly covalently bind that polypeptide. The resultant product could then be reactivated and a second (or plurality of) polypeptide(s) could be bound via the imine route such that it (they) would be released over time.

Such first polypeptides would include monoclonal antibodies that could be used as targeting moieties to a tissue of interest. In that instance, the second polypeptide could be one that functions as a toxin, for example, RNase, DNase and ricin. The monoclonal antibody would thus target the multiple conjugate molecule to the tissue of interest where the toxin would be proximately released for local effect.

Further contemplated herein is the formation of the linkage of a polyhistidine, which are known to be particularly good chelators, or other efficient chelator of metal ions, with subsequent hydrogenation to make the bond irreversible followed by the second step of forming further conjugation of the carrier with a biologically active polypeptide via the imine linkage described herein.

In order to provide for longer clearance rates of polypeptides so that the individual would be benefitted in vivo by the biological effects of the polypeptide factor in a more sustained fashion, it could be linked to a carrier via the imine linkage as described herein. It is known, for example, that hepatocyte growth factor is cleared via heparin binding. This could be inhibited by making the growth factor unavailable for such binding except over a predeterminable period of time.

One skilled in the art could list any of a number of further applications where the imine linkage as described herein could be used to advantage for the sustained release of an otherwise unmodified biologically active polypeptide as such in vivo. All such applications should be considered aspects of the present invention broadly covered by the scope of its terms.

The term "carrier" herein includes any of a number of molecules that bear or could be activated (oxidized) or otherwise treated so as to bear a reactive aldehyde group. A requirement for such a carrier would be that it be physiologically acceptable. For example, upon reaction of such a carrier via its reactive aldehyde group(s) with the biologically active polypeptide of interest, one may prefer to eliminate at least some residual unreacted aldehyde groups.

Thus, one could choose any of a number of compounds that would prove satisfactory in respect of the criteria listed above. One particularly attractive group of carriers would be polysaccharides, that could be preactivated by oxidative formation of reactive aldehyde groups, such as via periodate treatment, or that could be modified by introduction of primary amine groups. Dextran is an example. Dextran has the desirable property of being available in commercial form in different molecular weight distributions.

Dextran is a polymer of glucose containing vicinal diols which form aldehyde groups by reaction with an oxidizing agent such as periodate. Dextrans have the advantages as carriers of (1) high water solubility, (2) a well-defined and repetitive chemical structure, yielding many potential sites for binding or conjugation, (3) their availability in different molecular weight forms of from about $2 \times 10^3$ to $10^6$, and (4) low toxicity and low pharmacologic activity. See FIG. 13 infra.

Virtually any biologically active polypeptide, including those that are known and those that may be identified in future, can be used as a starting material for the formation of an adduct herein. In the preferred embodiment hereof for rapid sustained release, the conjugation would most probably occur with the aldehyde via the N-terminal amine of the polypeptide. However, it can be predicted that lysine or other amino acids along the backbone of the desired biologically active polypeptide could also so react forming conjugate molecules where there are one or more imine bonds of the biologically active polypeptide with the carrier molecule. One could foresee, for example, that arginine, and perhaps histidine, would also so bond with an aldehyde of the carrier starting material. Such multipoint attachment would produce a slow sustained release product.

Thus, the biologically active polypeptide of interest refers generally to small peptides as well as peptides having more than about 3 amino acids. The polypeptides may be bacterial, yeast, or most preferably, mammalian polypeptides. Examples of bacterial polypeptides include, e.g., alkaline phosphatase and β-lactamase. Examples of mammalian polypeptides include molecules such as, e.g., renin, a growth hormone, including human growth hormone, N-methionyl-human growth hormone (met-hGH), des-N-methionyl human growth hormone (hGH or rhGH), and bovine growth hormone; growth hormone releasing factor; parathyroid hormone; thyroid stimulating hormone; thyroid releasing hormone; thyroxine; lipoproteins; α1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial nuaturietic factor; lung surfactant; a plasminogen activator, such as urokinase or tissue-type plasminogen activator (t-PA); bombesin; thrombin; hemopoietic growth factor; tumor necrosis factor-alpha and -beta; enkephalinase; a serum albumin such as human serum albumin; muellerian-inhibiting substance; relaxin A-chain; relaxin B-chain; prorelaxin; mouse gonadotropin-associated peptide; a microbial protein, such as beta-lactamase; RNase; DNase; inhibin; activin; ricin; peptides such as polyhistidine; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); insulin-like growth factor binding proteins; CD proteins such as CD-3, CD-4, CD-8, and CD-19; erythropoietin; osteoinductive factors; immunotoxins; a bone morphogenetic protein (BMP); somatotropins; an interferon such as interferon-alpha, -beta, and -gamma; colony stimulating factors (CSFs), e.g., M-CSF, GM-CSF and G-CSF; interleukins (ILs), e.g., IL-1 to IL-10; superoxide bismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

It will be understood herein that the term "biologically active polypeptide" refers to a polypeptide that in its native environment inherently produces a biological effect or influence, notwithstanding it may not be (quite) so active in different environments, for example, when conjugated with carrier as described herein prior to its disassociation therefrom for use in unmodified form as such. However, the polypeptide may display full or substantially full biological activity when conjugated as described herein.

The preferred polypeptides of interest are human growth hormone; interferon-α, -β, or -γ; colony stimulating factors; tissue plasminogen activator; insulin-like growth factors such as IGF-1; CD4; erythropoietin; insulin-A or -B chain; factor VIII; human serum albumin; IL-2; hepatitis B vaccine; hepatocyte growth factor; vascular endothelial growth factor; nerve growth factor and DNase; it will be understood that this list is compiled based on current commercial activity and not necessarily because of particular facility in the system described herein.

DETAILED DESCRIPTION

General Procedures

The present invention is defined herein in terms of the formation of an imine conjugate upon reaction of an active aldehyde group(s) on a pharmaceutically acceptable carrier with a primary amine of a biologically active polypeptide. As mentioned herein, the choice of biologically active polypeptide is virtually infinite and includes those that are known and those that may become known in future.

As also mentioned herein, the choice of carrier molecule is also infinite within the confines of the criteria that it bear or is capable of being converted to bear active aldehyde (or primary amine) groups for reaction with the primary amine (or aldehyde) of the polypeptide and that it be itself pharmaceutically acceptable. Dextran is preferred.

In a stoichiometric reaction, the extent of oxidation and number of consequential aldehyde groups introduced into the dextran molecule may be controlled. Because the adduct formation is envisaged as an equilibrium reaction, the degree of oxidation is controlled, and amounts of reactants are used, such that an acceptable rate of breakdown of the adduct is observed in vivo.

Consequently, by controlling the degree of oxidation, one can control the number of conjugate reactions desired so that a sustained release can be predictive of a sustained overall dosage of the desired polypeptide in vivo. By use of such stoichiometric control, one can produce conjugates as sustained release pharmaceuticals that will have statistically predictable release of biologically active polypeptide over a statistically predictable period of time. Thus, one can fashion sustained release pharmaceuticals that could cover a rather broad range of treatment regimes, depending upon the age and size of the individual and the disease state being treated.

The compounding of such conjugates with pharmaceutical excipients is well within the skill of the art and would be chosen such as to form pharmaceutical compositions that are inherently physiologically acceptable.

Although the present invention is generic in concept, as defined above, the model system initially employed herein included use of a commercial form of dextran as the carrier, activation thereof by oxidation with periodate to form reactive aldehyde groups and human growth hormone as the biologically active polypeptide. Further research with additional biologically active polypeptides followed.

Notwithstanding the disclosure herein of the specific details of the initial model(s), it can be appreciated that one could arrive at the imine conjugates of the present invention following alternative, equivalent means other than those specifically described herein.

BRIEF DESCRIPTION OF THE DRAWINGS

FIG. 1 provides size exclusion chromatography (SEC) profiles for reaction between oxidized T40 dextran and met-hGH. Free (unbound) hGH elutes from 10–11.5 min. Reaction times of 21, 41 and 120 hours are shown. The separation was performed on a TSK 2000 SWXL column, 7.5 mm×30 cm. at ambient temperature. The solvent was 400 mM sodium phosphate, pH 7.8, flow rate was 1 mL/min and detection was 214 nm.

FIG. 2A illustrates SEC profile showing lack of reaction between non-oxidized dextran and met-hGH. No hGH-dextran complex is observed (elution time 5–9 min). Separation conditions are described in the legend to FIG. 1.

FIG. 2B illustrates SEC profile showing reaction between oxidized dextran and met-hGH (top). The lower profile shows lack of reaction between the same oxidized dextran that has been reduced ($NaBH_4$) before the addition of met-hGH. The separation conditions are described in the legend to FIG. 1. The lower molecular weight peaks at about 11 min. were not product related.

FIG. 3 illustrates SEC analysis for the reaction of oxidized dextran with rhGH (bottom profile). The top profile shows a similar analysis for free rhGH. The separation conditions are described in the legend to FIG. 1.

FIG. 4 illustrates SEC profile showing the preparative collection of the met-hGH-dextran complex. The complex was collected between 5.3–8.5 min. The separation conditions are described in the legend to FIG. 1.

FIG. 5 illustrates SEC analysis of the isolated complex collected in FIG. 4. The separation conditions are described in the legend to FIG. 1.

FIG. 6 illustrates SEC analysis of the isolated met-hGH-complex (shown in FIG. 5) after standing 2.5 days in 400 mM phosphate, pH 7.8. Met-hGH elutes at 9.5 to 10 min.

FIG. 7 depicts the body weight gains in hypophysectomized rats receiving two injections of the solutions indicated in the legend. The arrows indicate the times of the injections on days 1 and 4. Preparations 1 and 2 are rhGH-dextran complexes prepared as described previously and are identical except for an extra filtration step with the latter. rhGH means recombinant human growth hormone.

FIG. 8 depicts the body weight gains in hypophysectomized rats at day 4 after one injection of the solutions indicated in the legend. The * indicates a statistically significant increase compared to rhGH alone.

FIG. 9 depicts the weights of the spleen (left panel) and thymus (right panel) in hypophysectomized rats at sacrifice on day 5. The * indicates a statistically significant increase compared to rhGH alone.

FIG. 10 depicts the relative weights (expressed as a percentage of body weight) of the spleen (left panel) and thymus (right panel) in hypophysectomized rats at sacrifice on day 5. The * indicates a statistically significant increase compared to rhGH alone.

FIG. 11 depicts the width of the epiphyseal cartilage growth plate of the tibia in hypophysectomized rats at sacrifice on day 5. The * indicates a statistically significant increase compared to rhGH alone.

FIG. 12 depicts the serum levels of insulin like growth factor-1 (IGF-1: left panel) and human growth hormone (hGH: right panel) in the blood of hypophysectomized rats at sacrifice on day 5. The * indicates a statistically significant increase compared to rhGH alone.

FIG. 13 is a data sheet for the commercial product Dextran T40 by the manufacturer.

FIG. 14 depicts the formation of the adducts hereof graphically in respect of a particular embodiment.

EXAMPLES

1. Preparation of Sustained Release Imine Adduct Pharmaceuticals

The reversibility of adduct formation (equation 1) to give unmodified reactants is a major advantage.

(1) 

By appropriate selection of the R-group, the desired physical and chemical properties of the aldehyde and eventually the adduct can be selected. As a possible aldehyde "host", dextran was initially investigated.

Dextran has the desirable property of being available in different molecular weight distributions. In a stoichiometric reaction, the extent of oxidation and number of aldehyde groups introduced into the dextran molecule may be controlled. Since the adduct formation is envisaged as an equilibrium reaction, an excess of aldehyde groups relative to met-hGH, or any polypeptide, gives formation of the oxidized dextran-hGH complex. Furthermore, the degree of oxidation is chosen such that an acceptable rate of breakdown of the complex is observed in vivo.

To commercially available (Pharmacia), T40 DEXTRAN (See FIG. 13) ($0.125 \times 10^{-7}$ moles, approx. 250 glucose units/mole) in 200 mM sodium phosphate (700 µL), pH 4.5, sodium periodate ($2.34 \times 10^{-6}$ moles) was added. If complete reaction occurs, one would expect up to 4% of the glucose units to be oxidized to aldehydes. The reaction mixture was protected from light with aluminum foil and allowed to stand on ice. After 2 hours, the reaction was quenched with an excess of glycerol (50 µL, 10% glycerol), then desalted and buffer exchanged into 200 mM phosphate, pH 7,8, using NAP5 disposable G25 columns (Pharmacia).

The oxidation of dextran was qualitatively measured by iodometric titration or alternatively by monitoring the ability of the oxidized dextran to bind met-hGH. The amount of free and bound met-hGH was measured using size exclusion chromatography (SEC).

To the oxidized dextran (1 mg, 25 nmol; equivalent to 6.25 µmol of glucose monomers) in 200 mM sodium phosphate, pH 7.8 (400 µL) was added met-hGH (50 nmol). The reaction mixture was allowed to stand at room temperature and samples (20 µl) were removed and analyzed by SEC (FIG. 1). With time, a decrease in the amount of unbound hGH (retention time 10–12 min) was observed together with a corresponding increase in the amounts of higher molecular weight species (see FIG. 1) eluting between 5 and 9.5 min which was attributed to the dextran-hGH complex.

In contrast, no significant amount of higher molecular weight species were formed when non-oxidized dextran was reacted with met-hGH under similar conditions (FIG. 2A). In this analysis, unreacted met-hGH eluted at approximately 11 min.

As an additional control, the oxidized dextran was reduced with $NaBH_4$ (to eliminate aldehyde groups) and then reacted with met-hGH (same conditions as in FIG. 1). Again, no complex of higher molecular weight species were formed (FIG. 2B). In this analysis, met-hGH eluted at 10 min and the small peaks observed at 10.5 to 11.5 min were not product related.

A similar complex was observed when rhGH was incubated with oxidized dextran using the same conditions as for met-hGH. Analysis by SEC produced a similar profile of complexed and free rhGH (FIG. 3) to that was observed with met-hGH (FIG. 1).

The adduct of met-hGH and dextran was preparatively isolated and collected (FIG. 4). FIG. 5 shows SEC analysis of the pool and demonstrates that the complex is essentially free of unbound met-hGH. In fact, the small amount of met-hGH observed eluting at 10 min could have been formed by disassociation of the complex under the separation conditions. This dextran-met-hGH was submitted for amino acid analysis and the results are typical of those found for free met-hGH (Table 1).

TABLE 1

Amino Acid Analysis of Dextran-hGH Complex Isolated by Size Exclusion Chromatography (SEC)

| Amino Acid | Theoretical[a] | Dextran-hGH Complex |
|---|---|---|
| Asx[b] | 20 | 19.0 |
| Thr | 10 | 9 |
| Ser | 18 | 15.6 |
| Glx[c] | 27 | 26.8 |
| Pro + CySH | 8[d] | 7.9 |
| Gly | 8 | 64[f] |
| Ala | 7 | 7.5 |
| Val | 7 | 7.0 |
| Met | 4 | 3.2 |
| Ile | 8 | 7.3 |
| Leu | 26 | 25.5 |
| Tyr | 8 | 6.8 |
| Phe | 13 | 12.3 |
| His | 3 | 2.5 |
| Lys | 9 | 8.0 |
| Arg | 11 | 10.0 |
| Trp | 1 | ND |
| Cys | 4 | 2.3[g] |

[a]Theoretical amino acid composition of free met-hGH.
[b]Refers to the sum of asparagine and aspartic acid.
[c]Refers to the sum of glutamine and glutamic acid.
[d]Proline only.
[e]ND = not determined.
[f]Includes glycine from met-hGH formulation buffer.
[g]Sum of cysteic acid and half cysteine. Note coelution of CySH with Proline.

2. In vitro Confirmation of Structure

If the formation (and breakdown) of the dextran-hGH complex is an equilibrium reaction, then dilution of the complex with buffer should liberate free met-hGH.

Thus, the isolated dextran-met-HGH complex shown in FIG. 5, was allowed to stand at room temperature in SEC buffer (400 mM, sodium phosphate, pH 7.8) for 2.5 days and then analyzed. This analysis showed a significant peak (≈30% of total peak area) in the expected elution position for met-hGH, indicating breakdown of the complex.

3. In vivo Utility (Animal Studies)
MATERIALS AND METHODS
Preparation of activated dextran
(Further example of the general procedure)

Dextran T-40 was from Pharmacia, Sweden, and sodium periodate was from BDH, Uk. Oxidation buffer was sodium acetate, 100 mM, pH 4.5. All solutions were cooled to 0° C. on ice before oxidation started. A typical oxidation was carried out as follows: 10 millimoles of sodium periodate was added to 50 ml acetate buffer (at 0° C.) containing Dextran-T40 (8 mg/ml). The reaction was allowed to proceed with stirring for 35 minutes in the dark, at 4° C. Under these conditions, a 50% units of glucose activated dextran (UGAD) was obtained. Excess periodate was consumed with ethylene glycol. I. J. Goldstein, G. W. Hay, B. A. Lewis and F. Smith, *Methods in Carbohydrate Chemistry*, Vol. V., 367. A blank was prepared omitting the dextran solution. The reactive groups anchored to the dextran matrix were evaluated by the method of Fleury and Lange, using Convol grade (BDH) standards. P. Fleury and J. Lange, *J. Pharm. Chem.*, Vol. 17, 107, (1933); J. R. Dyer, *Methods Biochem. Anal.*, 3, 125, (1956).

Predictable levels of oxidation were achieved by manipulating the oxidation conditions.

The activated dextran can be stored up to 15 days in acetate buffer, 100 mM, pH 4.5, at 4° C.

Reversible attachment of rhGH to activated dextran
Example 1 (analytical study)

rhGH was provided by Genentech, Inc. Three vials of 5 mg. each were dissolved in 1.5 mls of MilliQ-water and buffer exchanged to sodium phosphate, 100 mM, pH 7.8 containing 0.01% sodium azide. At the same time two aliquots of dextran T-40, 18% and 50% UGAD respectively, were buffer exchanged to sodium phosphate 100 mM, sodium azide 0.01% pH 7.8 using a NAP-10 column (Pharmacia).

Three incubation vials were prepared:

a) Control: 0.68 ml of rhGH [4.4 mg/ml] plus 0.4 ml sodium phosphate buffer.

b) rhGH/18%UGAD: 0.68 ml of rhGH [4.4 mg/ml] plus 0.4 ml of dextran having a 18% UGAD [2.6 mg/ml].

c) rhGH/50%UGAD: 1.2 ml of rGH [4.4 mg/ml] plus 0.4 ml of dextran having a 50% UGAD [2.6 mg/ml].

The conjugation reaction was done in the dark at room temperature in a "Roto Torque" model #7637-01. Under these conditions equilibrium was reached at 40 hrs.

Preparation of Adduct for Animal Studies

Eight vials of 5 mg. each of rhGH were dissolved in 3.5 milliliters of MilliQ-water and buffer exchanged to sodium phosphate 100 mM, pH 7.8 using Sephadex G-15 packed in a Pharmacia 300×16 mm column. 36 mg. of protein was collected in 6 ml phosphate buffer.

4 milliliters of 52% UGAD containing a dextran concentration of 4 mg/ml were buffer exchanged to sodium phosphate 100 mM, pH 7.8, using Sephadex G-15, as described above. Elution in this case was detected using a Waters Differential Refractometer R401.

Activated dextran was collected at a concentration of 2.8 mg/ml. The reaction mixture was prepared as follows: 2.4 ml of activated dextran [2.8 mg/ml] was added to 6 ml of rhGH [6 mg/ml]. Incubation mixture was filtered using a Minisart NML SM 16534K (0.2 um) presterilized and nonpyrogenic filter (Sartorius) and incubated for 40 hrs, in the dark, at room temperature, using a "Roto Torque".

Isolation of rhGH-dextran complex from the reaction mixture and sodium cyanoborohydride reduction For analytical work, isolation was done using a Superdex 75 FPLC column. Large scale separation of the complex from the excess free hormone was performed on Sephadex G-50. In both cases the isolation buffer was PBS:139 mM sodium chloride, 12 mM of sodium phosphase, pH 7.4.

Aliquots of the isolated complex were reduced (to study the release process) with sodium cyanoborohydride in a two-fold concentration excess over protein. reduced and non-reduced aliquots were incubated at room temperature, in the dark, using a "Roto Torque" (rotating wheel).

Characterization of the Adduct

The fractions were analyzed (with or without cyanoborohydride reduction) by SDS-PAGE using a Pharmacia Phast system and by SEC using a Superdex-75 FPLC column (optimal separation range 3000 to 75000 for globular proteins) attached to a Pharmacia FPLC. A Waters Differential Refractometer R401 was connected in series to a UV-1 monitor for detection. The running buffer was PBS containing 0.01% sodium azide.

Pharmacokinetics
Purpose:

The aim of this study was to investigate the growth promoting anabolic effects of two preparations of a GH imine complex and compare the results to a comparable dose of rhGH or placebo in hypophysectomized rats.

Procedure:

Thirty-six female hypophysectomized SD rats were selected (Taconic Labs, Germantown, N.Y.) who fulfilled rat body weight baseline criteria (i.e. rats selected were weighed 3 times weekly for 3 weeks. Those selected weighed between 85–105 gm. and had a body weight change of <7 gm.).

Rats were placed into 6 groups of 6 rats per group and given two injections of the following, prepared as described above:

group 1 rhGH placebo 200 μg/rat equivalent group 2 rhGH-dextran imine complex 200 μg/rat group 3 rhGH-dextran imine complex 60 μg/rat group 4 rhGH-dextran imine complex 120 μg/rat group 5 rhGH-dextran imine complex 40 μg/rat group 6 rhGH 200 μg/rat Each rat received an injection volume of 100 μl to 200 μl depending upon the group and drug dilution. Injections were SQ at the nape of the neck on day 0 and again on day 4. Group 3 did not receive a second injection due to lack of reagents. Body weights were collected daily. At sacrifice on day 5 collections were made of spleen, thymus and liver for wet weights, tibia for epiphyseal plate measurements and serum for chemistry and hormone measurements.

Results:

Body weights (FIGS. 7 and 8)

The effect of rhGH injected by itself is transient in hypophysectomyal rats as demonstrated in this figure. The high dose dextran-HGH complex treated group showed a larger initial weight gain between days 1 and 2, a prolonged weight gain of 8 gm. over the 4 day period and an additional 6 gm. weight gain after the second injection. The weight gains after four days are shown in FIG. 8. The long lasting nature of the dextran-HGH complex (Prep 2) is shown by the persisting weight gain in the Prep 2-treated rats.

Organs (FIGS. 8 to 10)

Previously demonstrated was that spleen and thymus growth is dependent on the dose regime or pattern of administration of GH. See U.S. Pat. No. 5,202,119. An increase in spleen and thymus weight is a good indicator that there has been a continual presence of GH. These data show that rhGH every 4 days produced a small effect whereas the dextran-GH complex every 4 days produced a large effect on absolute spleen and thymus weight (FIG. 8). When spleen and thymus weight were expressed as a percentage of body weight the dextran GH complex had an effect and rhGH had no effect. These data show a continual presence of hGH in the animals given the dextran-hGH complex preparation.

Bone Growth (FIG. 11)

Epiphyseal tibial plate width is a sensitive measure of GH efficacy and good indicator of long bone growth. These data clearly show an increase in epiphyseal plate width in the dextran-HGH complex treated groups. rhGH showed a small stimulation of bone growth whereas the dextran HGH-complex group gave a more pronounced effect. The effect of 40 μg of dextran HGH-complex was greater than for 200 μg of rhGH alone.

Hormone levels (FIG. 12)

IGF-1 and hGH levels in the blood of the dextran-GH treated group were significantly increased at 24 hours post injection. (The concentrations of hGH have not bee corrected for assay dilution of 50-fold.) Note that in group 3, hGH appears to be detectable 5 days after one injection of the complex. In the Prep 2, 120 group, all samples gave greater than standard (GTS) values. This data confirms collectively that the dextran HGH-complex persists in the body and has the actions of a long lasting and long acting hGH.

Stability of the Adduct

The adduct can be frozen at −70° C. without losing its activity.

Sterilization of the Adduct

The development of a parenteral sustained release rhGH product was terminally sterilized by filtration through a Minisart NML SM 16534K (0.2 μm) presterilized and nonpyrogenic filter (Sartorius) before freezing the final product.

4. Additional Polypeptide Adduct Studies

These experiments detail progress using recombinant human Insulin-like Growth Factor-I (rHuIGF-I, IGF-I). Of the proteins studied, this was found to have the fastest kinetics of complex formation. The kinetics of complex formation were proportional to the % activation of the dextran sample used.

A trial incubation of IGF-I with a narrower MW distribution of activated dextran T-40 (i.e. sized T-40 dextran) was carried out.

This protein showed a good response to the conditions used in the incubations. All the incubations were carried out without rotation and shaking the samples. There is evidence of release in two different isolated complexes (rIGF-I/44% UGAD at 24 and at 48 hrs). The isolated peaks were both sharp, eluting in the void volume of the Superose column.

Study of CD4, rtPA and GP120-Dextran Adducts

Dextran used was T-40 activated by periodate oxidation to 26 and 52% units of glucose activated dextran (UCAD).

Five vials of CD4 at a concentration of 1 mg/ml, and were dialyzed against water using a Spectra/Por (MWO 3,500) membrane and freeze dried. 5 mgs of dried protein was dissolved in 0.5 ml. of MilliQ-water and buffer exchanged to sodium phosphate 100 mM, containing 0.02% sodium azide, pH 7.8.

Freeze dried rtPA (100 mg) was dissolved in 10 ml of milliQ-water, aliquoted and frozen at −20 ° C. Before use it was buffer exchanged into sodium phosphate as for C04.

GP120, 2.3 mg/ml in Tris buffer, was buffer exchanged into phosphate buffer as for CD4 and rtPA.

Incubation vials were prepared as described in the following Table.

| PROT. | SAMPLE | mg PROT. | mg DEXT. | PROT. CONC. | W/W | MOL/ MOL |
|---|---|---|---|---|---|---|
| CD4 | CONTROL | 1.2 | 0 | 0.95 | — | — |
| CD4 | 26% UGAD | 1.2 | 0.5 | 0.95 | 2.4 | 2.2 |
| CD4 | 52% UGAD | 1.2 | 0.5 | 0.95 | 2.4 | 2.2 |
| rtPA | CONTROL | 0.9 | 0 | 1 | — | — |
| rtPA | 26% UGAD | 1.8 | 0.5 | 1 | 3.6 | 2.2 |
| rtPA | 52% UGAD | 1.8 | 0.5 | 1 | 3.6 | 2.2 |
| GP120 | CONTROL | 0.65 | 0 | 0.6 | — | — |
| GP120 | 26% UGAD | 0.65 | 1.3 | 0.6 | 0.5 | 0.2 |
| GP120 | 52% UGAD | 0.65 | 1.3 | 0.6 | 0.5 | 0.2 |
| GP120 | 52% UGAD | 1.3 | 0.5 | 1 | 2.6 | 0.9 |

GP120 was incubated with an excess of dextran to protein to accelerate the complex formation process, thought to be slow or nil for a protein that carries a 50% glycosylation.

GP120-dextran adduct samples give an excellent example of how excess uncoupled dextran is distinguished in the RI detection system. The effect is enhanced for this particular case because dextran and this protein have different retention times.

Incubations were followed with SEC analysis using a Superose-12 column (with PBS as the running buffer) and SDS-PAGE gels. In some cases, results obtained with these techniques showed that all the protein was complexed at given incubation times. More protein was added to these samples, to saturate all aldehydes sterically available to protein.

All incubations were carried out on a rotating wheel, in the dark and at room temperature.

When complex was isolated from the 52% UGAD samples approximately 75% of the complexed protein was released in a period of 7 days. The released protein breaks down to give peaks of longer retention time.

There is a rapid release that occurs in the first hour after complex isolation. After this no significant CD4 elution peak was observed until 7 days. There is also an increase in breakdown products. Breakdown of the CD4 bands starts to be seen in the CD4 control of SDS-PAGE after 6 days incubation.

| | | rtPA-DEXTRAN ADDUCT STUDIES | | | | |
|---|---|---|---|---|---|---|
| PROT. | SAMPLE | mg PROT. | mg DEXT. | PROT. CONC. | W/W | MOL/ MOL |
| rtPA | CONTROL | 0.9 | 0 | 1 | — | — |
| rtPA | 26% UGAD | 1.8 | 0.5 | 1 | 3.6 | 2.2 |
| rtPA | 52% UGAD | 1.8 | 0.5 | 1 | 3.6 | 2.2 |

Incubation was carried out in the dark, at room temperature, in a rotation wheel.

SEC was performed (as for CD4 and GP120) using a Superose-12 column, with an optimal separation range of 1,000–300,000 Daltons and an exclusion limit for globular proteins of approximately 2,000,000 Daltons. The running buffer was PBS.

Without the arginine containing buffer, degradation of the protein occurs, especially when it is released.

After 40 hrs incubation more buffer exchanged rtPA (buffer exchanged the same day and kept at 4° C. until used) was added to the incubation samples.

Final protein/dextran ratios in incubation vials are:

| Sample | W/W | Mol/Mol |
|---|---|---|
| rtPA/26% UGAD | 6 | 3.7 |
| rtPA/52% UGAD | 8 | 5.2 |

In this study, rtPA was attached to activated dextran of 26% and 52% UGAD. Both incubations generated a high molecular weight complex that eluted with the void volume. When this peak was isolated, the rate of release was very similar in both cases After the first 24 hrs of incubation, little dextran complex formation was detected by SDS-PAGE. Therefore, more GP120 was added to the sample increasing the sample molar ratio to 1.4:1.

However, further complex did not form. This may be due to dextran dilution in this case. Gp120-dextran complex is detected in SEC as a shoulder on the uncoupled protein peak, making the isolation process difficult. SDS-PAGE also can not be used to judge the progress of complex formation since the main complex runs with the uncoupled protein.

GP120 should be coupled to dextran preferably with a molar ratio of no less than 4:1, protein:dextran. The dextran to be used should have a minimum activation of 50% UGAD.

Study of the rHGH-Dextran Adduct

Protein used was rHGH in three vials of 5 mg. each dissolved in 1.5 mls of MilliQ-water and buffer exchanged to sodium phosphate 100 mM, containing sodium azide 0.01%, pH 7.8. At the same time, two aliquots of dextran T-40, 18% and 50% UGAD respectively, were buffer exchanged to sodium phosphate 100 mM, azide 0.01%, pH 7.8 using a NAP-10 column. Three incubation vials were prepared:

a) control: 0.68 ml of rHGH [4.4 mg/ml] plus 0.4 ml sodium phosphate buffer.

b) rHGH/18%UGAD: 0.68 ml of rGH [4.4 mg/ml] plus 0.4 ml of 18% UGAD [2.6 mg/ml].

c) rHGH/50%UGAD: 1.2 ml of rGH [4.4mg/ml] plus 0.4 ml of 50% UGAD [2.6 mg/ml].

The vials were incubated on a rotating wheel at 2 revolutions per minute. The temperature was 16°–18° C. All samples were protected from light. After 40 hrs incubation, all samples were analyzed by SEC using a Superdex-75 FPLC column, with an optimal separation, range for globular proteins of 3,000–70,000 Daltons and exclusion limit of approx. 100,000 Daltons. The running buffer was PBS: 150 mM sodium chloride, 12 mM monosodium phosphate, containing 0.01% sodium azide, pH 7.4. The complex was isolated and analyzed immediately. Reduction of complex was with sodium cyanoborohydride in a 2 fold excess over protein. Reduced and non-reduced complexes were incubated at 16°–18° C. in the dark on a rotating wheel for 96 hrs. and analyzed by SDS-PAGE gel. Similarly, the released hGH was analyzed after 72 hr. release.

A two dimensional electrophoretic analysis was performed on the original rHGH/dextran incubation samples (8 days old). IEF was the first dimension and SDS, non-reduced PAGE in the second dimension. Two dimensional analyses were done this way to obtain results that could be compared with the one dimensional gels already obtained using the same samples.

The excess of protein used produces an hGH-complex from which an equilibrium state may be reached, and after complex isolation, protein release was obtained.

rHGH/18% UGAD complex sample:

This sample has 3 mg/ml protein and 1 mg/ml of dextran. Assuming that not less than 50% of the available protein has been complexed, one milliliter of this sample has 1.5 mg of complexed protein (slow release, different than the free protein that will be cleared fast from the circulation).

An injection to a rat of 0.5 ml will deliver 0.75 mg of complexed protein and 0.5 mg of dextran. The release of this sample in vitro was 13%. This would give a release of 0.098 mg of protein per day over a period of 7.6 days.

rHGH/50% UGAD complex sample:

This sample also has 3 mg/ml of protein and 0.63 mg/ml of dextran. Assuming the same percentage of protein coupling as before, 0.5 ml of this sample will deliver to the rat 0.5 mg of complexed protein and 0.32 mg dextran.

This complex releases 6.5% of protein in vitro. That would release 0.030 mg of protein per day for a period of 16.6 days.

Pharmaceutical Compositions

The reader is directed to literature extant that supplies relevant details as to devising pharmaceutically acceptable compositions and administration methodology for the efficacious treatment of disease states. For example, the usual administration would be by subcutaneous injection or intramuscular, however the imine complexed polypeptides might be administered by many routes. For example, they might be incorporated into oral dosing devices, into devices for the transcutaneous delivery of polypeptides or incorporated into implantable biodegradable implants or prostheses that are surgically implanted.

Clinical Administration

Drug entities prepared as described above for specific clinical use are compounded in accord with known techniques to produce useful pharmaceutical compositions that are pharmaceutically acceptable for appropriate administration.

Such drugs are tested for safety, dose response and efficacy in humans as per federal regulations. Ordinary studies conducted pursuant to those regulations shall determine the safety and efficacious dose regimens appropriate in the circumstances for treatment of the particular indication of concern. The attendant clinical studies are in the area of routine experimentation generally within the ken of the art-skilled. These drugs are administered via standard formulations to patients for such medications, again either topically, orally, parenterally, rectally, alone or in combination, at regular intervals or as a single bolus, or as a continuous infusion, and so forth.

For example, a typical pharmaceutical composition containing the active compound human growth hormone hereof together with an appropriate pharmaceutically acceptable carrier entity(ies) may be in the range of about 0.7 mg to about 70 mg per dose for a 70 kg man, and an exposure of 10 days. This would give an average daily dose of about 0.001 mg/kg/day to about 1 mg/kg/day per kilogram of body weight. The regulatory protocols necessary to produce marketable drug entities provide the exact dosage and the details of the pharmaceutically acceptable form of a compound of this invention.

The information contained in the part hereof supra entitled "Pharmacokinetics" are materials and methods and results of animal in vivo studies using the model system. These protocols and results are believed to be translatable with routine experiments by the art-skilled to related adducts hereof into any animal, and hence, a human being.

Concluding Remarks

The foregoing description details specific methods that can be employed to practice the present invention. Having detailed specific methods initially used to characterize, prepare sustained release pharmaceuticals and use the compositions thereof, and further disclosure as to specific model systems, those skilled in the art will well enough know how to devise alternative reliable methods for arriving at the same information and for extending this information to other systems. Thus, however detailed the foregoing may appear in text, it should not be construed as limiting the overall scope hereof; rather, the ambit of the present invention is to be governed only by the lawful construction of the appended claims.

We claim:

1. A sustained release pharmaceutical composition comprising a pharmaceutically acceptable excipient admixed with a sustained release pharmaceutical imine bond adduct of a dextran carrier and a biologically active polypeptide, wherein said imine bond is formed by reaction of a reactive aldehyde group with a primary amine under non-reducing conditions and wherein said biologically active polypeptide is hGH or N-methionyl hGH.

2. A sustained release pharmaceutical composition comprising a pharmaceutically acceptable excipient admixed with a sustained release pharmaceutical imine bond adduct of a dextran carrier and a biologically active polypeptide, wherein said imine bond is formed by reaction of a reactive aldehyde group with a primary amine under non-reducing conditions and wherein said biologically active polypeptide is IGF-1.

3. A sustained release pharmaceutical composition comprising a pharmaceutically acceptable excipient admixed with a sustained release pharmaceutical imine bond adduct of a dextran carrier and a biologically active polypeptide, wherein said imine bond is formed by reaction of a reactive aldehyde group with a primary amine under non-reducing conditions and wherein said biologically active peptide is t-PA.

* * * * *